(12) United States Patent
Chuang et al.

(10) Patent No.: US 10,894,853 B2
(45) Date of Patent: Jan. 19, 2021

(54) FURAN-MODIFIED COMPOUND AND OLIGOMER

(71) Applicant: INDUSTRIAL TECHNOLOGY RESEARCH INSTITUTE, Chutung (TW)

(72) Inventors: Kuei-Yi Chuang, Hsinchu (TW); Kuo-Chan Chiou, Tainan (TW); Feng-Po Tseng, Taoyuan (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 133 days.

(21) Appl. No.: 16/179,296

(22) Filed: Nov. 2, 2018

(65) Prior Publication Data

US 2019/0144410 A1 May 16, 2019

Related U.S. Application Data

(60) Provisional application No. 62/580,483, filed on Nov. 2, 2017.

(51) Int. Cl.

| | | |
|---|---|---|
| C08F 277/00 | (2006.01) | |
| C08L 101/06 | (2006.01) | |
| C08G 73/06 | (2006.01) | |
| C08G 65/40 | (2006.01) | |
| C08G 73/12 | (2006.01) | |
| C08G 65/44 | (2006.01) | |
| C08L 71/00 | (2006.01) | |
| C08L 71/12 | (2006.01) | |
| C07D 307/42 | (2006.01) | |
| C07D 307/52 | (2006.01) | |
| C07D 407/06 | (2006.01) | |
| C08G 18/02 | (2006.01) | |
| C08G 18/83 | (2006.01) | |
| C08G 61/04 | (2006.01) | |
| C08G 61/10 | (2006.01) | |
| C08G 61/12 | (2006.01) | |
| C08G 65/331 | (2006.01) | |
| C08F 267/04 | (2006.01) | |
| C08F 283/08 | (2006.01) | |
| C08F 283/10 | (2006.01) | |
| C08F 299/02 | (2006.01) | |

(52) U.S. Cl.
CPC .......... *C08F 277/00* (2013.01); *C07D 307/42* (2013.01); *C07D 307/52* (2013.01); *C07D 407/06* (2013.01); *C08F 267/04* (2013.01); *C08F 283/08* (2013.01); *C08F 283/10* (2013.01); *C08F 299/022* (2013.01); *C08G 18/022* (2013.01); *C08G 18/831* (2013.01); *C08G 61/04* (2013.01); *C08G 61/10* (2013.01); *C08G 61/124* (2013.01); *C08G 65/3318* (2013.01); *C08G 65/40* (2013.01); *C08G 65/44* (2013.01); *C08G 73/0655* (2013.01); *C08G 73/126* (2013.01); *C08L 71/00* (2013.01); *C08L 71/126* (2013.01); *C08L 101/06* (2013.01); *C08F 2500/02* (2013.01); *C08F 2810/40* (2013.01); *C08G 2261/149* (2013.01); *C08G 2261/1646* (2013.01)

(58) Field of Classification Search
CPC .. C07D 307/52; C07D 307/42; C07D 407/06; C08G 18/022; C08G 18/831; C08G 65/3318; C08G 61/04; C08G 2261/149; C08G 61/10; C08G 2261/1646; C08G 61/124
USPC ........................................................ 524/111
See application file for complete search history.

(56) References Cited

U.S. PATENT DOCUMENTS

| 8,734,939 B2 | 5/2014 | Herr et al. |
|---|---|---|
| 2012/0082840 A1 | 4/2012 | Herr et al. |

(Continued)

FOREIGN PATENT DOCUMENTS

| CN | 103842415 A | 6/2014 |
|---|---|---|
| CN | 104045810 A | 9/2014 |
| TW | 201609848 A | 3/2016 |

OTHER PUBLICATIONS

Shibata et al., Polymer Journal, 43, 455-463, 2011. (Year: 2011).*

(Continued)

*Primary Examiner* — Hui H Chin
(74) *Attorney, Agent, or Firm* — Birch, Stewart, Kolasch & Birch, LLP

(57) ABSTRACT

The invention provides a furan-modified compound or oligomer. The compound has a structure represented by Formula I:

[Formula I]

$$A \!-\!\!\left[\!G\!-\!\!\text{CH}_2\!-\!\!\underset{\text{furan}}{\bigcirc}\!\right]_x$$

When formula I represents a compound, x is an integer of 1~5; A including a group formed of ketone, amido, imide, imido, phenyl ether or enol ether group; G is a direct bond, $-O-$, $-N-$, $-Ar-NH-(CH_2)_b-$, $-Ar-O-(CH_2)_b-$, $-Ar-O-(CH_2)_a-NH-(CH_2)_b-$, $-(CH_2)_a-NH-(CH_2)_b-$, $-(CH_2)_a-O-(CH_2)_b-$ or $-(CH_2)_a-CH(OH)-(CH_2)_b-NH-$; Ar is substituted or unsubstituted arylene group; a is an integer of 1 to 5; and b is an integer of 0 to 5.

3 Claims, No Drawings

(56) References Cited

U.S. PATENT DOCUMENTS

| | | |
|---|---|---|
| 2012/0261064 A1 | 10/2012 | Boday et al. |
| 2013/0245204 A1 | 9/2013 | Pastine et al. |
| 2014/0262192 A1 | 9/2014 | Boday et al. |
| 2017/0226271 A1 | 8/2017 | Makal et al. |

OTHER PUBLICATIONS

Masutani et al., Sen'i Gakkaishi, 68(3), 64-72, 2012. (Year: 2012).*
Ishida et al., Polymer, 52, 2877-2882, 2011. (Year: 2011).*
Ishida et al., Polymer Degradation and Stability, 110, 149-155, 2014. (Year: 2014).*
Japanese Office Action for Japanese Application No. 2018-207798, dated Nov. 26, 2019, with English translation.
Zuen et al., "Crystalline furanic polyisocyanates," Polymer Bulletin, vol. 26, No. 4, 1991, pp. 383-390 (7 pages total).
Shibata et al., "High-performance hybrid materials prepared by the thermo-reversible Diels-Alders polymerization of fufuryl ester-terminated butylene succinate oligomers and maleimide compounds," Polymer Journal, vol. 43, 2011, pp. 455-463.
Chen et al., "Characterization of thermally reworkable thermosets: materials for environmentally friendly processing and reuse", Polymer 2002, vol. 43, pp. 131-139.
Wertz et al., "Thermally Conductive-Silicone Composites with Thermally Reversible Cross-links", ACS Appl. Mater. Interfaces 2016, pp. 13669-13672.

\* cited by examiner

FURAN-MODIFIED COMPOUND AND OLIGOMER

This application claims the benefit of U.S. provisional application Ser. No. 62/580,483, filed Nov. 2, 2017, the disclosure of which is incorporated by reference herein in its entirety.

TECHNICAL FIELD

The disclosure relates in general to a compound and an oligomer, and more particularly to a furan-modified compound and an oligomer.

BACKGROUND

At the end of 2015, European union published Circular Economy Package (CEP). The compositions and components of products in future should meet the requirements of being repairable, durable, and recyclable to achieve circular economy. In addition, the Paris Agreement in 2016 proposed to reduce greenhouse gas emission and keeping a global average temperature below 2° C. above pre-industrial levels.

Of the elements of conventional electronic products, printed circuit boards (PCBs) are responsible for the most $CO_2$ emissions, e.g. over 100000 kg $CO_2$/10000 $m^2$ PCB. As such, the related industries are encountering the challenges of efficiently recycling waste PCBs to lower $CO_2$ emissions, while simultaneously obeying the energy related ecodesign directives. The conventional method of recycling a waste PCB is to crush it and then purifying or burying the metal and plastic in a landfill. However, the recycling ratio is usually lower than 3%. Therefore, in practice, waste PCBs still get incinerated, which may produce a lot of $CO_2$ and contribute to the greenhouse effect. The skill of purifying metal has matured in recent years, and 130 kg of copper, 19 kg of tin, and about 16 ounce of gold can be refined from 1 ton of PCBs today. However, a PCB contains about 54.5% of plastic, which is the major $CO_2$ emission source. The plastic in a PCB includes insulation resin and glass fiber cloth. All the conventional resin systems for PCBs belong to thermosetting polymer, which has stable properties and is therefore difficult to recycle. Although decomposable thermoplastic polymer is provided, the glass transfer temperature, the thermal cracking temperature, and the flame resistance of the thermoplastic polymer should be improved even further, in order to achieve the properties of the conventional insulation resin in PCB.

Not only the PCB, the resin composition used in other products that need to withstand high temperatures during process or use also encounters the similar challenge when the demands of recycling wastes is increased. Therefore, there is a need to adjust the ingredients of a resin composition with similar properties to render it capable for use in a high temperature environment and can also be recycled easily.

SUMMARY

According to an embodiment of the present invention, a furan-modified compound is provided. The furan-modified compound has a structure represented by Formula I:

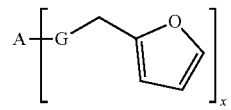

[Formula I]

wherein, x is an integer of 1 to 5; A is a group including ketone group, amido group, imide group, imido group, phenyl ether group or enol ether group; G is a direct bond, —O—, —N—, —Ar—NH—$(CH_2)_b$—, —Ar—O—$(CH_2)_b$—, —Ar—O—$(CH_2)_a$—NH—$(CH_2)_b$—, —$(CH_2)_a$—NH—$(CH_2)_b$—, —$(CH_2)_a$—O—$(CH_2)_b$— or —$(CH_2)_a$—CH(OH)—$(CH_2)_b$—NH—; Ar is substituted or unsubstituted arylene group; a is an integer of 1 to 5; and b is an integer of 0 to 5.

According to an embodiment of the present invention, a furan-modified oligomer is provided. The furan-modified oligomer has a structure represented by Formula II:

[Formula II]

wherein, y is an integer of 1 to 5; B is a repeating group including amine group, amide group, maleimide group, ester group, phenyl ether group or enol ether group; D is a direct bond, —O—, —N—, —$Ar_2$—NH—$(CH_2)_d$—, —$Ar_2$—O—$(CH_2)_d$—, —$Ar_2$—O—$(CH_2)_c$—NH—$(CH_2)_d$—, —$(CH_2)_c$—NH—$(CH_2)_d$—, —$(CH_2)_c$—O—$(CH_2)_d$— or —$(CH_2)_c$—CH(OH)—$(CH_2)_d$—NH—; $Ar_2$ is substituted or unsubstituted arylene group; c is an integer of 1 to 5; and d is an integer of 0 to 5. The furan-modified oligomer has a number average molecular weight from 1000 to 12000.

BRIEF DESCRIPTION OF THE DRAWINGS

N/A

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details.

According to an embodiment of the present invention, a furan-modified compound is provided. The furan-modified compound has a structure represented by Formula I:

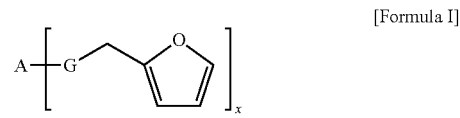

[Formula I]

wherein, x is an integer of 1 to 5, A is a group including ketone group, amido group, imide group, imido group, phenyl ether group or enol ether group; G is a direct bond, —O—, —N—, —Ar—NH—$(CH_2)_b$—, —Ar—O—$(CH_2)_b$—, —Ar—O—$(CH_2)_a$—NH—$(CH_2)_b$—, —$(CH_2)_a$—NH—$(CH_2)_b$—, —$(CH_2)_a$—O—$(CH_2)_b$— or —$(CH_2)_a$—$CH(OH)$—$(CH_2)_b$—$NH$—; Ar is substituted or unsubstituted arylene group; a is an integer of 1 to 5; and b is an integer of 0 to 5.

In some embodiments of the disclosure, A can be

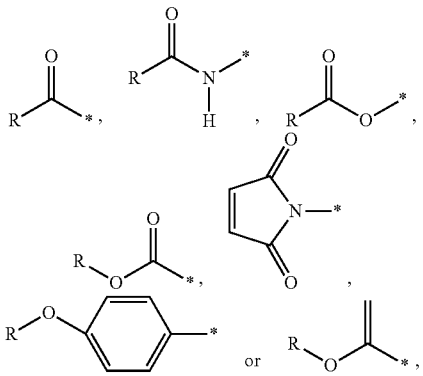

R is hydrogen, halogen, $C_1$~$C_8$ alkyl, $C_1$~$C_8$ haloalkyl, $C_1$~$C_{10}$ cycloalkyl, or $C_6$~$C_{12}$ aryl group; and A is connected to G at position represented by asterisk (*). More specifically, R can be hydrogen, fluorine, methyl, ethyl, propyl, isopropyl, n-butyl, second butyl, isobutyl, t-butyl, pentyl, hexyl, fluorine methyl, fluorine ethyl, cyclopentyl, cyclohexyl, phenyl, biphenyl, or naphthyl. For example, A can be

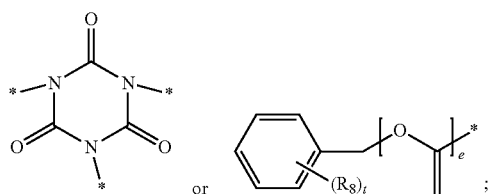

and A is connected to G at position represented by asterisk (*), wherein $R_8$ is $CH_3$ or $C_2H_5$, t is an integer of 1 to 5, e is an integer of 1 to 5.

According to an embodiment of the present disclosure, Ar is substituted or unsubstituted phenylene, biphenylene, naphthylene, thienylene, indolylene, phenanthrenylene, indenylene, anthracenylene, or fluorenylene group. Specifically, Ar can be phenylene, diphenylene, naphthylene, thienylene, indolylene, phenanthrenylene, indenylene, anthracenylene, or fluorenylene group with substitution groups of one to four $C_1$~$C_6$ alkyl groups.

In an embodiment of the present invention, a furan-modified oligomer is provided. The furan-modified oligomer has a structure represented by Formula II:

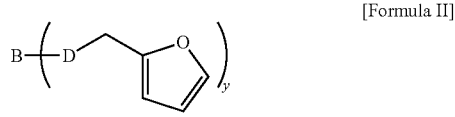

[Formula II]

wherein, y is an integer of 1 to 5, B is a repeating group including of amine, amide, maleimide, ester group, phenyl ether or enol ether group; D is a direct bond, —O—, —N—, —$Ar_2$—$NH$—$(CH_2)_d$—, —$Ar_2$—$O$—$(CH_2)_d$—, —$Ar_2$—$O$—$(CH_2)_c$—$NH$—$(CH_2)_d$—, —$(CH_2)_c$—$NH$—$(CH_2)_d$—, —$(CH_2)_c$—$O$—$(CH_2)_d$— or —$(CH_2)_c$—$CH(OH)$—$(CH_2)_d$—$NH$—; $Ar_2$ is substituted or unsubstituted arylene; c is an integer of 1 to 5; and d is an integer of 0 to 5. The furan-modified oligomer has a number average molecular weight from 1000 to 12000.

For example, B can be

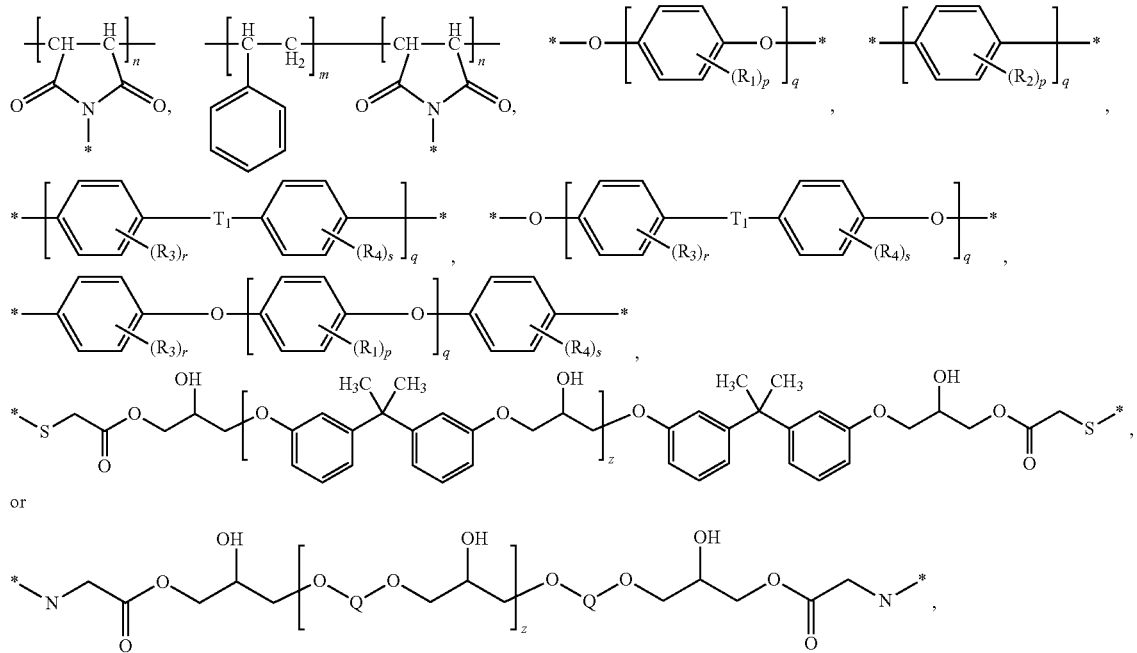

wherein B is connected to D at position represented by asterisk (*); m is an integer of 7 to 200; n is an integer of 7 to 200; each of p, r and s is an integer of 1 to 5; q is an integer of 5 to 50; z is an integer of 5 to 20; each of $R_1$, $R_2$, $R_3$, $R_4$ is independently $C_1$-$C_5$ alkyl; $T_1$ is a direct bond, $C_1$~$C_{12}$ linear or branched alkyl, —O—, —S— or —NH—; Q is

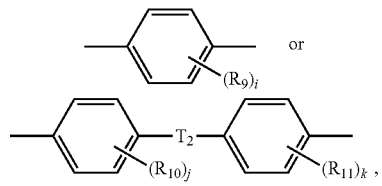

wherein, each of $R_9$, $R_{10}$ and $R_{11}$ is independently $CH_3$ or $C_2H_5$, $T_2$ is $C_1$~$C_{12}$ linear or branched alkyl, and each of i, j and k is an integer of 1 to 5.

According to an embodiment of the present disclosure, $Ar_2$ is substituted or unsubstituted phenylene, biphenylene, naphthylene, thienylene, indolylene, phenanthrenylene, indenylene, anthracenylene, or fluorenylene. Specifically, $Ar_2$ can be phenylene, diphenylene, naphthylene, thienylene, indolylene, phenanthrenylene, indenylene, anthracenylene, or fluorenylene with substitution groups of one to four $C_1$~$C_6$ alkyl groups.

A number of exemplary embodiments and comparison examples are provided below to make the furan-modified compound and/or the oligomer and the application thereof better understood. The disclosure below is exemplified by reversible cross-linking reaction composition and the composite material formed of the reversible cross-linking reaction composition.

Preparation Examples of Furan-Modified Compound and/or Oligomer

Oligomer Having a Structure Represented by Formula I-1

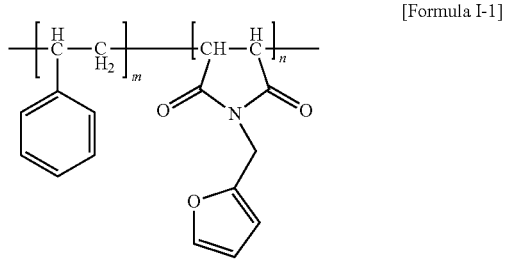

In Formula I-1, m was 7~200, n was 7~200, and the oligomer had a number average molecular weight of 2000~12000.

Example 1

60 grams of styrene maleic anhydride (SMA, purchased from the Polyscope, the weight average molecular weight (Mw) is 7500) was added to and dissolved in 80 grams of dimethylacetamide (DMAc, purchased from the Echo Chemical) solvent. Then, 29.6 grams of furfurylamine (FA, purchased from the Aldrich Chemical) was added to the solution, and then heated to 100° C.~160° C. and stirred to react. After completing the reaction, the solution was cooled down to room temperature, and an oligomer having a structure represented by Formula I-1 was obtained. Then, the physical properties of oligomer were measured, as shown in Table 1.

Example 2

60 grams of styrene maleic anhydride (SMA, purchased from the Polyscope, the weight average molecular weight (Mw) is 9000) was added to and dissolved in 80 grams of dimethylacetamide (DMAc) solvent. Then, 22.33 grams of furfurylamine (FA, purchased from the Aldrich Chemical) was added to the solution, and then heated to 100° C.~160° C. and stirred to react. After completing the reaction, the solution was cooled down to room temperature, and an oligomer having a structure represented by Formula I-1 is obtained. Then, the physical properties of oligomer were measured, as shown in Table 1.

Example 3

83 grams of styrene maleic anhydride (SMA, purchased from the Polyscope, the weight average molecular weight (Mw) is 10000) was added to and dissolved in 115 grams of dimethylacetamide (DMAc) solvent. Then, 40 grams of furfurylamine (FA, purchased from the Aldrich Chemical) was added to the solution, and then heated to 100° C.~160° C. and stirred to react. After completing the reaction, the solution was cooled down to room temperature, and an oligomer having a structure represented by Formula I-1 was obtained. Then, the physical properties of the oligomer were measured, as shown in Table 1.

Analysis of Properties and Results

The oligomers prepared in Examples 1 to 3 were analyzed by reflection IR spectroscopy (Spectrum One-54415, PERLIN ELMER) to measure their IR spectra. In the IR spectra data, the —$CO_2NH$ character peaks of 1701 $cm^{-1}$ and 1776 $cm^{-1}$ mean that the furfurylamine was grafted on the styrene maleic anhydride to form the maleimide functional group. The C—O—C character peaks of 1006 $cm^{-1}$ and 1068 $cm^{-1}$ and the C=C character peak of 1491 $cm^{-1}$ mean the signals of furan group in the furfurylamine. In addition, the oligomers prepared in Examples 1 to 3 were analyzed by differential scanning calorimeter (Q10, TA Instrument Co., Ltd.) under the standard IPC-TM-650.2.4.24 to measure their glass transfer temperature (Tg), as tabulated in Table 1. The oligomers prepared in Examples 1 to 3 were also analyzed by gel permeation chromatography (RI 830, JASCO) to measure their weight average molecular weight (Mw), as tabulated in Table 1.

TABLE 1

| | Compositions | | | Characteristics | |
| --- | --- | --- | --- | --- | --- |
| | SMA | | | | |
| | Mw | (g) | FA (g) | Tg (° C.) | Mw |
| Example 1 | 7,500 | 60 | 29.6 | 121 | 8,700 |
| Example 2 | 9,000 | 60 | 22.33 | 112 | 10,500 |
| Example 3 | 10,000 | 83 | 40 | 103 | 11,800 |

Oligomer Having a Structure Represented by Formula I-2

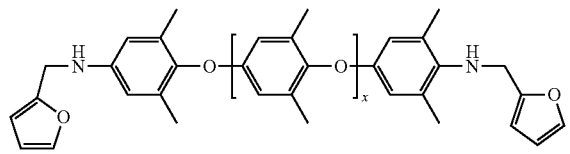

[Formula I-2]

In Formula I-2, x was 5~47; and the oligomer had a number average molecular weight of 1000~6000.

Example 4

60 grams of polyphenylene ether (PPE, purchased from the Sabic, Mn: 1600) was added to and dissolved in 60 grams of dimethylacetamide (DMAc) solvent. Then, 6.9 grams of furfurylamine (FA, purchased from the Aldrich Chemical) was added to the solution, and then heated to 100° C.~160° C. and stirred to react. After completing the reaction, the solution was cooled down to room temperature, and an oligomer having a structure represented by Formula I-2 was obtained. Then, the physical properties of the oligomer were measured, as shown in Table 2.

Example 5

60 grams of polyphenylene ether (PPE, purchased from the Sabic, Mn: 2350) was added to and dissolved in 60 grams of dimethylacetamide (DMAc) solvent. Then, 8 grams of furfurylamine (FA, purchased from the Aldrich Chemical) was added to the solution, and then heated to 100° C.~160° C. and stirred to react. After completing the reaction, the solution was cooled down to room temperature, and an oligomer having a structure represented by Formula I-2 was obtained. Then, the physical properties of oligomer were measured, as showed in Table 2.

Analysis of Properties and Results

The oligomers prepared in Examples 4 and 5 were analyzed by reflection IR spectroscopy (Spectrum One-54415, PERLIN ELMER) to measure their IR spectra. In the IR spectra data, the NH character peak of 3200 $cm^{-1}$ to 3400 $cm^{-1}$ means that the furfurylamine was grafted on the polyphenylene ether. The C—O—C character peaks of 1006 $cm^{-1}$ and 1068 $cm^{-1}$ and the C=C character peak of 1491 $cm^{-1}$ mean the signals of furan group in the furfurylamine. In addition, the oligomers prepared in Examples 4 and 5 were analyzed by differential scanning calorimeter (Q10, TA Instrument Co., Ltd.) under the standard IPC-TM-650.2.4.24 to measure their glass transfer temperature (Tg), as tabulated in Table 2. The oligomers prepared in Examples 4 and 5 were also analyzed by gel permeation chromatography (RI 830, JASCO) to measure their weight average molecular weight (Mw), as tabulated in Table 2.

TABLE 2

| | Compositions | | | Characteristics | |
| --- | --- | --- | --- | --- | --- |
| | PPE | | | | |
| | Mw | (g) | FA (g) | Tg (° C.) | Mw |
| Example 4 | 1,600 | 60 | 6.9 | 142 | 3,850 |
| Example 5 | 2,350 | 60 | 8 | 152 | 5,210 |

Oligomer Having a Structure Represented by Formula I-3

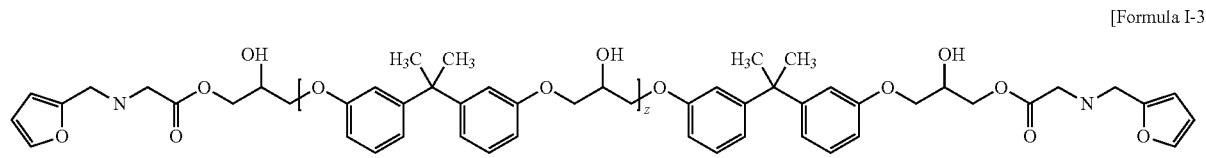

[Formula I-3]

In formula I-3, z was 5~20 and the oligomer had a number average molecular weight of 900~3000.

Example 6

50 grams of epoxy acrylate oligomer (DOUNLE-MER1730, purchased from the Double Bond Chemical) was added to 60 grams of dimethylacetamide (DMAc) solvent. Then, 10 grams of furfurylamine (FA, purchased from the Aldrich Chemical) was added to the solution, and then heated to 100° C.~140° C. and stirred to react. After completing the reaction, the solution was cooled down to room temperature, and an oligomer having a structure represented by Formula I-3 was obtained. Then, the physical properties of the oligomer were measured, as showed in Table 3.

Analysis of Properties and Results

The oligomer prepared in Example 6 was analyzed by reflection IR spectroscopy (Spectrum One-54415, PERLIN ELMER) to measure its IR spectrum. In the IR spectrum data, the NH character peak of 3200 $cm^{-1}$ to 3400 $cm^{-1}$ means that the furfurylamine was grafted on the epoxy acrylate oligomer. The C—O—C character peaks of 1006 $cm^{-1}$ and 1068 $cm^{-1}$ and the C=C character peak of 1491 $cm^{-1}$ mean the signals of furan group in the furfurylamine. In addition, the oligomer prepared in Example 6 was analyzed by differential scanning calorimeter (Q10, TA Instrument Co., Ltd.) under the standard IPC-TM-650.2.4.24 to measure its glass transfer temperature (Tg), as tabulated in Table 3. The oligomer prepared in Example 6 was also analyzed by gel permeation chromatography (RI 830, JASCO) to measure its weight average molecular weight (Mw), as tabulated in Table 3.

TABLE 3

| | Compositions | | | Characteristics |
|---|---|---|---|---|
| | Epoxy acrylate oligomer | | | |
| | Mn | (g) | FA (g) | Tg (° C.) | Mw |
| Example 6 | ~850 | 60 | 8.5 | 125.3 | ~927 |

Compound Having a Structure Represented by Formula I-4

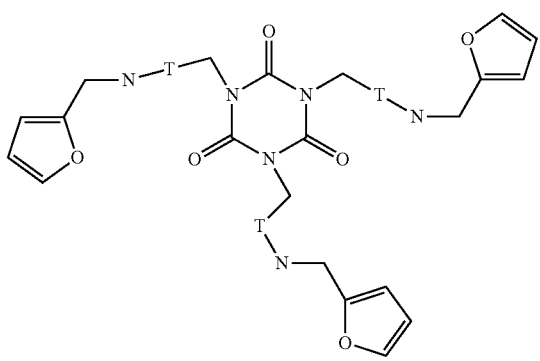

[Formula I-4]

In Formula I-4, T is —CH$_2$—CH(OH)-group or —CH$_2$—CH$_2$-group.

Example 7

50 grams of triallyl isocyanurate (TAIC, purchased from the Aldrich Chemical) was added to 60 grams of dimethylacetamide (DMAc) solvent. Then, 19.48 grams of furfurylamine (FA, purchased from the Aldrich Chemical) was added to the solution, and then heated to 100° C.~160° C. and stirred to react. After completing the reaction, the solution was cooled down to room temperature, and a compound having a structure represented by Formula I-4 was obtained.

Example 8

50 grams of tris (2,3-epoxy propyl) isocyanurate (TEPIC, purchased from the Nissan Chemical) was added to 60 grams of dimethylacetamide (DMAc) solvent. Then, 23 grams of furfurylamine (FA, purchased from the Aldrich Chemical) was added to the solution, and then heated to 100° C.~160° C. and stirred to react. After completing the reaction, the solution was cooled down to room temperature, and a compound having a structure represented by Formula I-4 was obtained.

Analysis of Properties and Results

The compounds prepared in Examples 7 and 8 were analyzed by reflection IR spectroscopy (Spectrum One-54415, PERLIN ELMER) to measure their IR spectra. In the IR spectra data, the NH character peak of 3200 cm$^{-1}$ to 3400 cm$^{-1}$ means that the furfurylamine was grafted on the triallyl isocyanurate or the tris(2,3-epoxy propyl) isocyanurate. The C—O—C character peaks of 1006 cm$^{-1}$ and 1068 cm$^{-1}$ and the C=C character peak of 1491 cm$^{-1}$ mean the signals of furan group in the furfurylamine. In addition, the compounds prepared in Examples 7 and 8 were analyzed by differential scanning calorimeter (Q10, TA Instrument Co., Ltd.) under the standard IPC-TM-650.2.4.24 to measure their glass transfer temperature (Tg), as tabulated in Table 4.

TABLE 4

| | Compositions | | | Characteristics |
|---|---|---|---|---|
| | TAIC (g) | TEPIC (g) | FA (g) | Tg (° C.) |
| Example 7 | 50 | 0 | 19.48 | 143.17 |
| Example 8 | 0 | 50 | 23 | 152 |

Preparation Examples of Recyclable Resin Composition

Recyclable Resin Compositions Including Single Type of Furan-Modified Oligomer

Example 9

100.47 grams of the oligomer having a structure represented by Formula I-1 synthesized in example 1 and 50 grams of bismaleimide compound BMI-1000 (purchased from K.I. Chemical Industry; the molecular weight: 358.35) were reacted at 50° C.~60° C. for 30 minutes to form a varnish (reversible cross-linking reaction composition). Then, the varnish was put in an oven and reacted at 170° C.~190° C. to obtain cross-linked composition I.

Example 10

271.2 grams of the oligomer having a structure represented by Formula I-2 synthesized in example 4 and 50 grams of BMI-1000 (purchased from K.I. Chemical Industry) were reacted at 50° C.~60° C. for 30 minutes to form a varnish (reversible cross-linking reaction composition). Then, the varnish was put in an oven and reacted at 170° C.~190° C. to obtain cross-linked composition II.

Example 11

40.18 grams of the oligomer having a structure represented by Formula I-1 synthesized in example 1 and 10 grams of BMI-1000 (purchased from K.I. Chemical Industry) were reacted for 30 minutes at 50° C.~60° C. to form a varnish (reversible cross-linking reaction composition). Then, the varnish was put in an oven and reacted at 170° C.~190° C. to obtain cross-linked composition III.

Example 12

108.4 grams of the oligomer having a structure represented by Formula I-2 synthesized in example 4 and 10 grams of BMI-1000 (purchased from K.I. Chemical Industry) were reacted for 30 minutes at 50° C.~60° C. to form a varnish (reversible cross-linking reaction composition). Then, the varnish was put in an oven and reacted at 170° C.~190° C. to obtain cross-linked composition IV.

Example 13

50.24 grams of the oligomer having a structure represented by Formula I-1 synthesized in example 1 and 50 grams of BMI-1000 (purchased from K.I. Chemical Industry) were reacted for 30 minutes at 50° C.~60° C. to form a varnish (reversible cross-linking reaction composition). Then, the varnish was put in an oven and reacted at 170° C.~190° C. to obtain cross-linked composition V.

Example 14

135.6 grams of the oligomer having a structure represented by Formula I-2 synthesized in example 4 and 50 grams of BMI-1000 (purchased from K.I. Chemical Industry) were reacted for 30 minutes at 50° C.~60° C. to form a varnish (reversible cross-linking reaction composition). Then, the varnish was put in an oven and reacted at 170° C.~190° C. to obtain cross-linked composition VI.

Analysis of Properties and Results

The cross-linked compositions I to VI prepared in Examples 9 to 14 were analyzed by reflection IR spectroscopy (Spectrum One-54415, PERLIN ELMER) to measure their IR spectra. In the IR spectra data, the original BMI-1000 character peak of 822 $cm^{-1}$ disappeared after the reaction, and the signal intensity of the C—O—C character peak on the furan group of 1068 $cm^{-1}$ was obviously lowered, which means that the cross-linked products were formed. In addition, the cross-linked compositions I to VI prepared in Examples 9 to 14 were analyzed by differential scanning calorimeter (Q10, TA Instrument Co., Ltd.) under the standard IPC-TM-650.2.4.24 to measure their glass transfer temperature (Tg), as tabulated in Table 5. The cross-linked compositions I to VI prepared in Examples 9 to 14 were respectively sampled as 5 mg and analyzed by differential scanning calorimeter (Q10, TA Instrument Co., Ltd.), in which each of the samples was heated to 350° C. at a heating rate of 5° C./min to measure the reversible crosslinking temperature (Tr) of the cross-linked compositions I to VI prepared in Examples 9 to 14, as tabulated in Table 5. As seen in the reversible crosslinking temperature (Tr) in Table 5, the cross-linked compositions in Examples were stable at a high temperature of at least 160° C. and were still stable even at a temperature above 260° C.

TABLE 5

| | Composition | | | | Properties | |
|---|---|---|---|---|---|---|
| | (a) furan-group-containing oligomer (g) | | (b) bismaleimide (g) | (a)/(b) Molar ratio | Tg (° C.) | Tr (° C.) |
| | Formula (I-1) | Formula (I-2) | BMI-1000 | | | |
| Example 9 | 100.47 | | 50 | 1/1 | 168 | 230 |
| Example 10 | | 271.2 | 50 | 1/1 | 154 | 230 |
| Example 11 | 40.18 | | 10 | 2/1 | 175 | 220 |
| Example 12 | | 108.4 | 10 | 2/1 | 168 | 230 |
| Example 13 | 50.24 | | 50 | 1/2 | 145 | 180 |
| Example 14 | | 135.6 | 50 | 1/2 | 132 | 161 |

Compositions Including Multiple Types of Furan-Modified Compound and/or Oligomer Example 15

54.24 grams of the oligomer having a structure represented by Formula I-1 synthesized in example 1, 135.6 grams of the oligomer having a structure represented by Formula II-2 synthesized in example 4 and 50 grams of BMI-1000 (purchased from K.I. Chemical Industry) were reacted at 50° C.~60° C. for 30 minutes to form a varnish (reversible cross-linking reaction composition). Then, the varnish was put in an oven and reacted at 170° C.~190° C. to obtain cross-linked composition VII.

Example 16

54.24 grams of the oligomer having a structure represented by Formula I-1 synthesized in example 1, 42.38 grams of the compound having a structure represented by Formula I-4 synthesized in example 7 and 50 grams of BMI-1000 (purchased from K.I. Chemical Industry) were reacted at 50° C.~60° C. for 30 minutes to form a varnish (reversible cross-linking reaction composition). Then, the varnish was put in an oven and reacted at 170° C.~190° C. to obtain cross-linked composition VIII.

Example 17

135.6 grams of the oligomer having a structure represented by Formula I-2 synthesized in example 4, 42.38 grams of the compound having a structure represented by Formula I-4 synthesized in example 7 and 50 grams of BMI-1000 (purchased from K.I. Chemical Industry) were reacted at 50° C.~60° C. for 30 minutes to form a varnish (reversible cross-linking reaction composition). Then, the varnish was put in an oven and reacted at 170° C.~190° C. to obtain cross-linked composition IX.

Example 18

33.5 grams of the oligomer having a structure represented by Formula I-1 synthesized in example 1, 90.4 grams of the oligomer having a structure represented by formula (I-2) synthesized in example 4, 28.3 grams of the compound having a structure represented by Formula I-4 synthesized in example 7 and 50 grams of BMI-1000 (purchased from K.I. Chemical Industry) were reacted at 50° C.~60° C. for 30 minutes to form a varnish (reversible cross-linking reaction composition). Then, the varnish was put in an oven and reacted at 170° C.~190° C. to obtain cross-linked composition X.

Analysis of Properties and Results

The cross-linked compositions VII to X prepared in Examples 15 to 18 were analyzed by reflection IR spectroscopy (Spectrum One-54415, PERLIN ELMER) to measure their IR spectra. In the IR spectra data, the original C═C character peak on BMI-1000 of 822 $cm^{-1}$ disappeared after the reaction, and the signal intensity of the C—O—C character peak on the furan group of 1068 $cm^{-1}$ was obviously lowered, which means that the cross-linked products were formed. In addition, the cross-linked compositions VII to X prepared in Examples 15 to 18 were analyzed by differential scanning calorimeter (Q10, TA Instrument Co., Ltd.) under the standard IPC-TM-650.2.4.24 to measure their glass transfer temperature (Tg), as tabulated in Table 6. The cross-linked compositions VII to X prepared in Examples 15 to 18 were respectively sampled as 5 mg and analyzed by differential scanning calorimeter (Q10, TA Instrument Co., Ltd.), in which each of the samples was heated to 350° C. at a heating rate of 5° C./min to measure the reversible crosslinking temperature (Tr) of the cross-linked compositions VII to X prepared in Examples 15 to 18, as tabulated in Table 6. As seen in the reversible crosslinking temperature (Tr) of Table 6, the cross-linked compositions in Examples could be stable at a high temperature of at least 160° C. and is still stable at a temperature above 300° C.

TABLE 6

| | (a) furan-group-containing oligomer (g) | | | (b) bismalei-mide | (a)/ | Properties | |
|---|---|---|---|---|---|---|---|
| | Formula (I-1) | Formula (I-2) | Formula (III-1) | BMI-1000 | (g) (b) molar ratio | Tg (° C.) | Tr (° C.) |
| Example 15 | 54.24 | 135.6 | | 50 | 1/1 | 185 | 200 |
| Example 16 | 54.24 | | 42.38 | 50 | 1/1 | 169 | 250 |
| Example 17 | | 135.6 | 42.38 | 50 | 1/1 | 251 | 300 |
| Example 18 | 33.5 | 90.4 | 28.3 | 50 | 1/1 | 237 | 290 |

Test and Result of Reversible Reaction

The cross-linked compositions I to X prepared in Examples 9 to 18 were crushed. The cross-linked compositions were heated to about 250° C.~300° C. to crack the crosslinking bondings and reverse back to varnish state, and then cooled to 60° C.~80° C. to further harden to bulks. The bulks were analyzed by reflection IR spectroscopy (Spectrum One-54415, PERLIN ELMER) to measure their IR spectra. In the IR spectra data, the original C=C character peak on BMI-1000 of 822 $cm^{-1}$ reappeared, and the signal intensity of the C—O—C character peak on the furan group of 1068 $cm^{-1}$ was obviously enhanced, which means that the crosslinking bondings of the cross-linked compositions were cracked, thereby recovering back to the compositions of furan group-containing oligomer and/or compound and BMI-1000.

Discussion on the Results of Analysis

For the reversible crosslinking reactant compositions in Examples, the two maleimide groups of the bismaleimide compound could react with the furan groups of two furan group-containing oligomer or compound through the 1,2-addition reaction. When the steric structure achieved a specific temperature, the bondings formed from the 1,2-addition reaction would be cracked, thereby breaking the bridge between the furan group-containing oligomer/compound and the bismaleimide compound for recovering back to original reactants. The above properties are beneficial to recycle and reuse the compositions. According to the result of the Examples, the reversible crosslinking reactant compositions of the disclosure had a stable structure, high thermal resistance, and high reversible temperature, which were beneficial for use in high-temperature processes. For example, the composition serving as the insulation resin material for PCB should be intact during the reflow process, such that the reversible temperature of the composition was preferably higher than or equal to 250° C.

Synthesis and Analysis of Composite Material

Example 19

33.5 grams of the oligomer having a structure represented by Formula I-1 synthesized in example 1, 90.4 grams of the oligomer having a structure represented by formula (I-2) synthesized in example 4, 28.3 grams of the compound having a structure represented by Formula I-4 synthesized in example 7, and 50 grams of BMI-1000 (purchased from K.I. Chemical Industry) were added to 75 grams of dimethylacetamide (DMAc) solvent, and reacted at 50° C.~60° C. for 30 minutes to form a varnish. A glass fiber cloth was impregnated in the varnish, and then backed at 140° C.~170° C. to prepare a prepreg. The prepregs were laminated with copper foil to form copper clad laminate.

Comparative Example 100 wt % of Epoxy resin 828 (BE-188, commercially available from Chang Chun Chemical Co., Ltd.), 5 phr of dicyandiamide (commercially available from Echo Chemical Co., Ltd), and 500 ppm of 2-methylimidazole (2-MI, commercially available from Echo Chemical Co., Ltd.) were added to methyl ethyl ketone (MEK, commercially available from Echo Chemical Co., Ltd) to prepare a varnish with a solid content of 70%. A glass fiber cloth was impregnated in the varnish, and then backed at 170° C. to prepare a prepreg. The prepregs were laminated with copper foil to form copper clad laminate. The lamination process was performed at a temperature of 170° C.~190° C. for 1 hours to 2 hours under a pressure of 350 psi-450 psi. The prepared copper clad laminate was FR-4 plate for general PCB.

Analysis of Properties and Results

The copper clad laminates in Examples 19 and Comparative Example were analyzed by differential scanning calorimeter (Q10, TA Instrument Co., Ltd.) under the standard IPC-TM-650.2.4.24 to measure their glass transfer temperature (Tg), as tabulated in Table 7. The copper clad laminates in Examples 19 and Comparative Example were analyzed by thermomechanical analyzer (Q400, TA Instrument Co., Ltd.) under the standard IPC-TM-650.2.4.24 to measure their coefficient of thermal expansion (CTE), as tabulated in Table 7. The copper clad laminates in Examples 19 and Comparative Example were analyzed by thermogravimetric analysis (Q500, TA Instrument Co., Ltd.) under the standard IPC-TM-650 2.3.40 to measure their degradation temperature (Td), as tabulated in Table 7. The copper clad laminates in Examples 19 and Comparative Example were respectively sampled as 5 mg and analyzed by differential scanning calorimeter (Q10, TA Instrument Co., Ltd.), in which each of the samples was heated to 350° C. at a heating rate of 5° C./min to measure the reversible crosslinking temperature (Tr) of the copper clad laminates in Examples 19 and Comparative Example, as tabulated in Table 7. The copper clad laminates in Examples 19 and Comparative Example were analyzed by resonant cavity type microwave dielectrometer (AET company, Japan) under the standard JIS-compliant 1641 to measure their dielectric constant (Dk) and dissipation factor (Df), as tabulated in Table 7. As shown in Table 7, the copper clad laminates in Example 19 and Comparative Example had similar dielectric constant and similar dissipation factor. Compared to Comparative Example, the copper clad laminate in Example 19 had a reversible crosslinking temperature of 300° C. The resin in the copper clad laminate in Example 19 can be reversible cross-linked by heating to about 300° C., thereby forming the furan-group-containing oligomer and/or compound and the bismaleimide compound for being recycled.

TABLE 7

| | Tg (° C.) | XY-CTE (ppm/° C.) | Td (° C.) | Tr (° C.) | Dk | Df |
|---|---|---|---|---|---|---|
| Example 19 | 180~212 | 16~20 | 360 | 300 | 3.75 | 0.012 |
| Comparative example | 140 | 30 | 350 | n/a | 4.2 | 0.015 |

Reversible Reaction Test and Result

The copper clad laminate in Example 19 was etched to remove the copper foils, and then put into a solution of about 250° C. to 300° C. to dissolve and recycle the composition. The recycled resin composition was collected and analyzed by reflection IR spectroscopy (Spectrum One-54415, PERLIN ELMER) to measure its IR spectrum. In the IR spectrum data, the C=C character peak on BMI-1000 of 822 cm$^{-1}$ reappeared, and the signal intensity of the C—O—C character peak on the furan group of 1068 cm$^{-1}$ was obviously enhanced, which means that the crosslinking bondings of the resin compositions were cracked, thereby recovering back to the original furan group-containing oligomer or compound and BMI-1000. In addition, the recycled resin composition was cured again, and the cured resin composition had the same Tg as that of the cured original resin composition (Example 18). It further proves that the composite material in Example 19 can be recycled to be reused.

Discussion on the Results of Analysis

The composites prepared by methods of Examples included reversible crosslinking reactant compositions, thereby increasing the recycling ratio of the composites. For example, utilizing the compositions with a reversible crosslinking temperature higher than or equal to 250° C. may improve the recycling ratio of PCB, therefore reducing the $CO_2$ emission amounts. In addition, the recycled compositions can be repeatedly used as the insulation resin during fabricating PCB or sub-quality raw material for achieving the circular economy.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A furan-modified oligomer having a structure represented by Formula II:

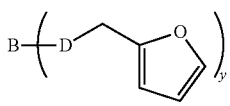

[Formula II]

wherein, y is an integer of 1 to 5; D is a direct bond, —O—, —Ar$_2$—NH—(CH$_2$)$_d$—, —Ar$_2$—O—(CH$_2$)$_d$—, —Ar$_2$—O—(CH$_2$)$_c$—NH—(CH$_2$)$_d$—, —(CH$_2$)$_c$—NH—(CH$_2$)$_d$—, —(CH$_2$)$_c$—O—(CH$_2$)$_d$— or —(CH$_2$)$_c$—CH(OH)—(CH$_2$)$_d$—NH—; Ar$_2$ is substituted or unsubstituted arylene group; c is an integer of 1 to 5; and d is an integer of 0 to 5, wherein the furan-modified oligomer has a number average molecular weight from 1000 to 12000;

wherein B is

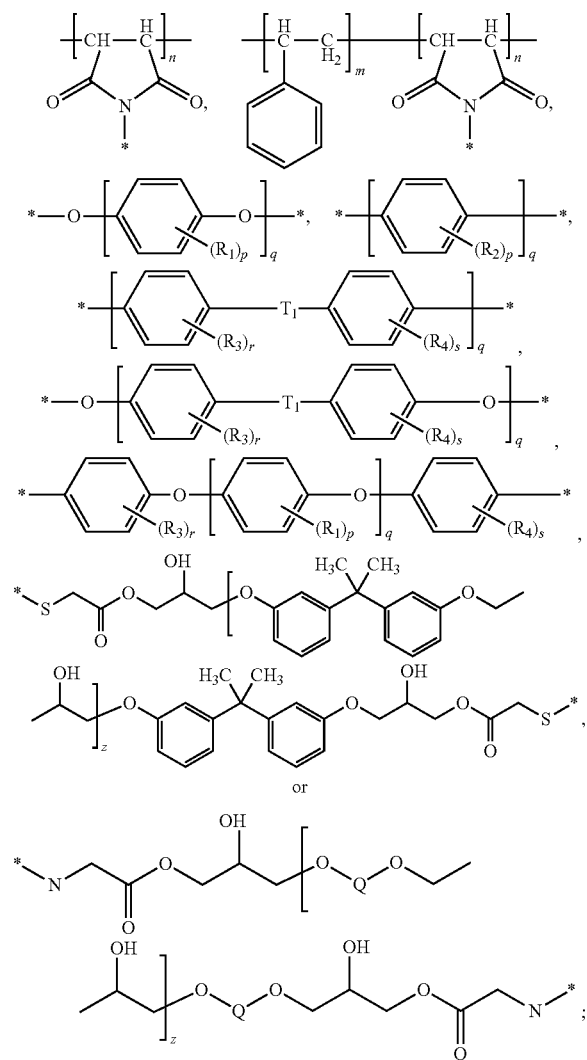

B is connected to D at position represented by asterisk (*); m is an integer of 7 to 200; n is an integer of 7 to 200; each of p, r and s is an integer of 1 to 5; q is an integer of 5 to 50; z is an integer of 5 to 20; each of R$_1$, R$_2$, R$_3$, R$_4$ is independently C$_1$-C$_5$ alkyl; T$_1$ is a direct bond, C$_1$-C$_{12}$ linear or branched alkyl, —O—, —S— or —NH—; Q is

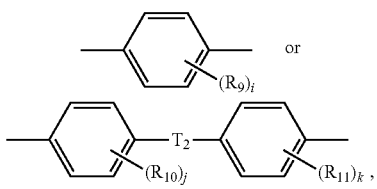

wherein, each of R$_9$, R$_{10}$ and R$_{11}$ is independently CH$_3$ or C$_2$H$_5$, T$_2$ is C$_1$-C$_{12}$ linear or branched alkyl, and each of i, j and k is an integer of 1 to 5.

2. The furan-modified oligomer according to claim 1, wherein Ar$_2$ is substituted or unsubstituted phenylene, biphenylene, naphthylene, thienylene, indolylene, phenanthrylene, indenylene, anthrylene, or fluorenylene group.

3. The furan-modified oligomer according to claim 1, wherein $Ar_2$ is phenylene, biphenylene, naphthylene, thienylene, indolylene, phenanthrylene, indenylene, anthrylene, or fluorenylene group with substitution groups of one to four $C_1$-$C_6$ alkyl groups.

* * * * *